US009402587B2

United States Patent
Allmendinger et al.

(10) Patent No.: US 9,402,587 B2
(45) Date of Patent: Aug. 2, 2016

(54) METHOD FOR RECORDING PROJECTIONS DURING A SPIRAL SCAN, METHOD FOR IMAGING AND MULTI-SLICE COMPUTED TOMOGRAPHY DEVICE

(71) Applicant: Siemens Aktiengesellschaft, Munich (DE)

(72) Inventors: Thomas Allmendinger, Forchheim (DE); Winrich Heidinger, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 72 days.

(21) Appl. No.: 14/325,419

(22) Filed: Jul. 8, 2014

(65) Prior Publication Data
US 2015/0043708 A1 Feb. 12, 2015

(30) Foreign Application Priority Data
Aug. 9, 2013 (DE) .......................... 10 2013 215 807

(51) Int. Cl.
*A61B 6/03* (2006.01)
*A61B 6/00* (2006.01)
(Continued)

(52) U.S. Cl.
CPC ................. *A61B 6/032* (2013.01); *A61B 6/027* (2013.01); *A61B 6/0407* (2013.01); *A61B 6/06* (2013.01);
(Continued)

(58) Field of Classification Search
CPC .......... A61B 6/027; A61B 6/032; A61B 6/06; A61B 6/54; A61B 6/0407; A61B 6/0457; A61B 6/547; A61B 6/5205; A61B 6/42
See application file for complete search history.

(56) References Cited

U.S. PATENT DOCUMENTS 5,442,675 A * 8/1995 Swerdloff ................ A61B 6/00
378/150
6,072,851 A * 6/2000 Sivers ..................... A61B 6/032
378/15
(Continued)

FOREIGN PATENT DOCUMENTS

CN 1518954 A 8/2004
CN 1636513 A 7/2005
(Continued)

OTHER PUBLICATIONS

Stierstorfer Karl et al., "Weighted FBP—a simple approximate 3D FBP algorithm for multislice spiral CT with good dose usage for arbitrary pitch", in: Phys. Med. Biol., vol. 49, 2004, pp. 2209-2218, DOI: 10.1088/0031-9155/49/11/007.
(Continued)

*Primary Examiner* — Glen Kao
(74) *Attorney, Agent, or Firm* — Harness, Dickey & Pierce, P.L.C.

(57) ABSTRACT

In an embodiment, a method includes at least moving a patient table through a measurement region of the computed tomography device, the movement of the patient having at least one phase of variable speed during the projection recording, time-solved determination or recording of the patient table position, time-resolved recording of projections of at least one part of an examination object moving with the table, the number of the slices contributing to the recording being varied during the at least one phase of variable speed of the patient table as a function of the table speed in such a way that the quotient formed from the current table speed divided by the number of the slices contributing to the recording is constant so that the pitch factor is kept constant during the projection recording, and time-resolved determination or recording of the number or slices contributing to the projection recording.

25 Claims, 6 Drawing Sheets

(51) Int. Cl.
*A61B 6/02* (2006.01)
*A61B 6/04* (2006.01)
*A61B 6/06* (2006.01)

(52) U.S. Cl.
CPC ............... *A61B 6/42* (2013.01); *A61B 6/5205* (2013.01); *A61B 6/54* (2013.01); *A61B 6/547* (2013.01); *A61B 6/0457* (2013.01)

(56) References Cited

U.S. PATENT DOCUMENTS

| | | | |
|---|---|---|---|
| 7,848,790 B2 * | 12/2010 | Pan | A61B 6/032 378/15 |
| 7,978,810 B2 | 7/2011 | Schwarz et al. | |
| 2004/0120451 A1 * | 6/2004 | Tsukagoshi | A61B 6/032 378/4 |
| 2005/0074085 A1 * | 4/2005 | Hsieh | A61B 5/055 378/4 |
| 2005/0245803 A1 * | 11/2005 | Glenn, Jr. | A61B 5/4255 600/407 |
| 2005/0248503 A1 | 11/2005 | Schobben et al. | |
| 2006/0177002 A1 * | 8/2006 | Toth | A61B 6/032 378/150 |
| 2007/0030947 A1 * | 2/2007 | Popescu | A61B 6/022 378/19 |
| 2010/0054395 A1 | 3/2010 | Noshi et al. | |
| 2011/0255657 A1 * | 10/2011 | Noordhoek | A61B 6/032 378/11 |

FOREIGN PATENT DOCUMENTS

| | | |
|---|---|---|
| CN | 1675085 A | 9/2005 |
| CN | 1767787 A | 5/2006 |
| CN | 1846620 A | 10/2006 |
| CN | 101664317 A | 3/2010 |
| CN | 102245107 A | 11/2011 |
| DE | 102007021023 A1 | 11/2008 |
| WO | WO 2014037253 A1 | 3/2014 |

OTHER PUBLICATIONS

German Office Action mailed Feb. 25, 2014.
Office Action for corresponding Chinese Application No. 201410387941.5 dated Feb. 29, 2016 and English translation thereof.

* cited by examiner

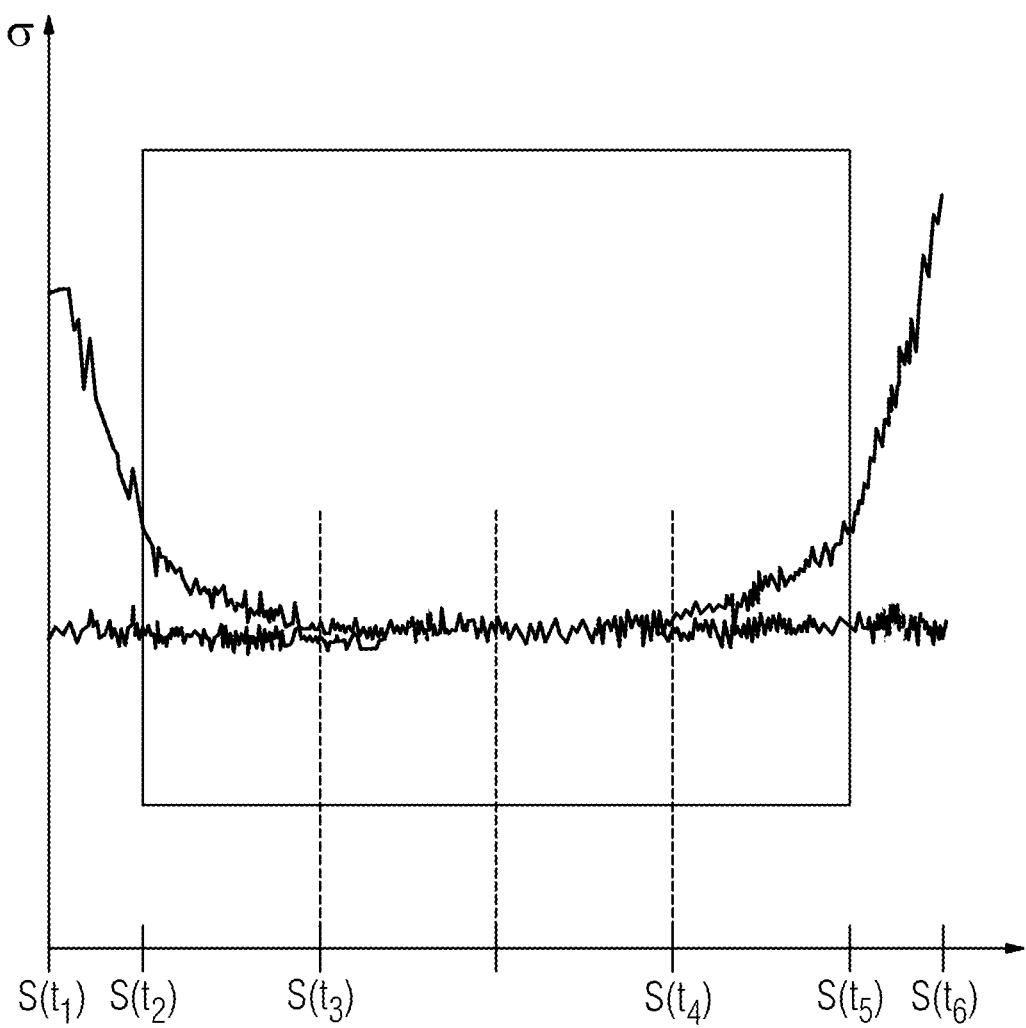

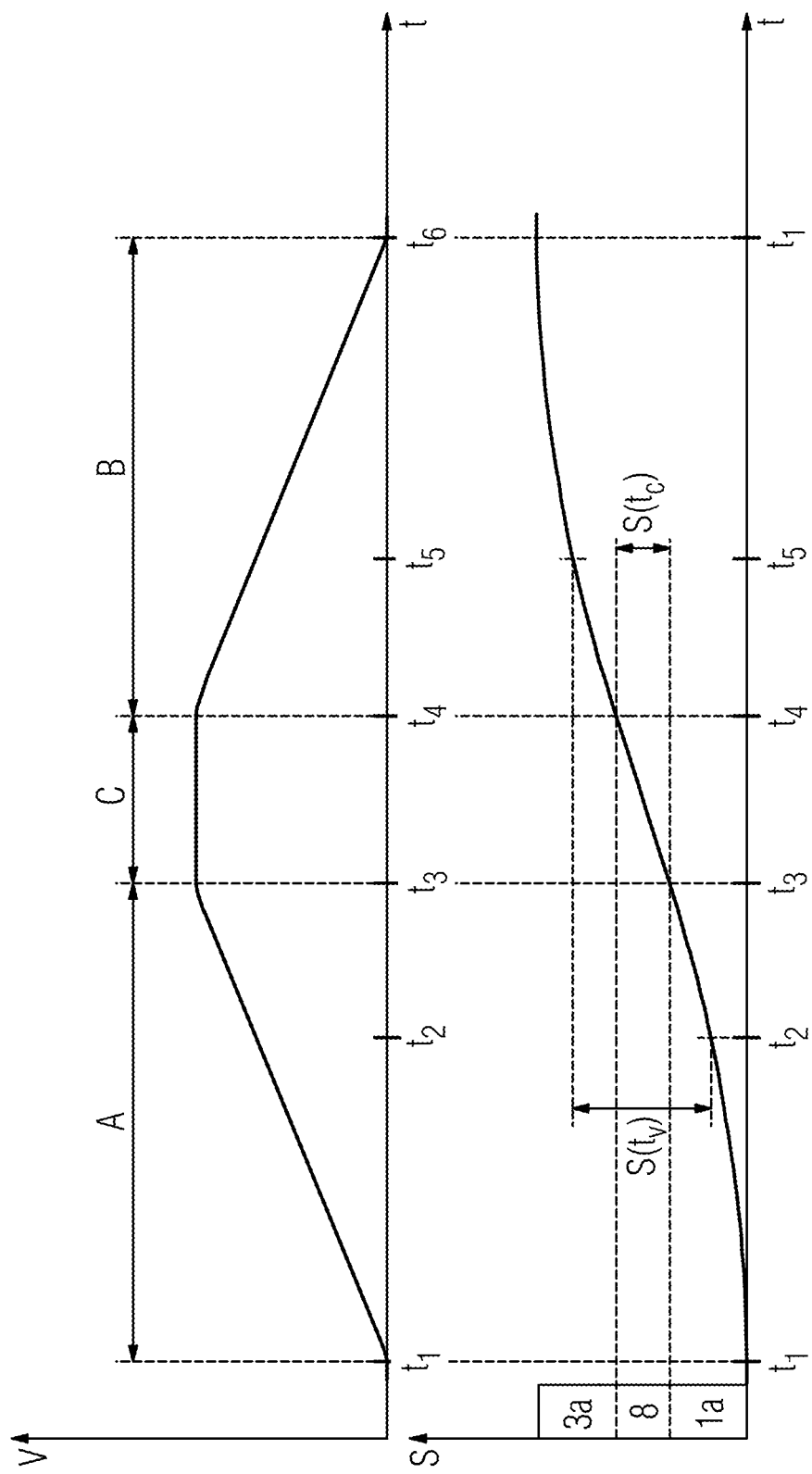

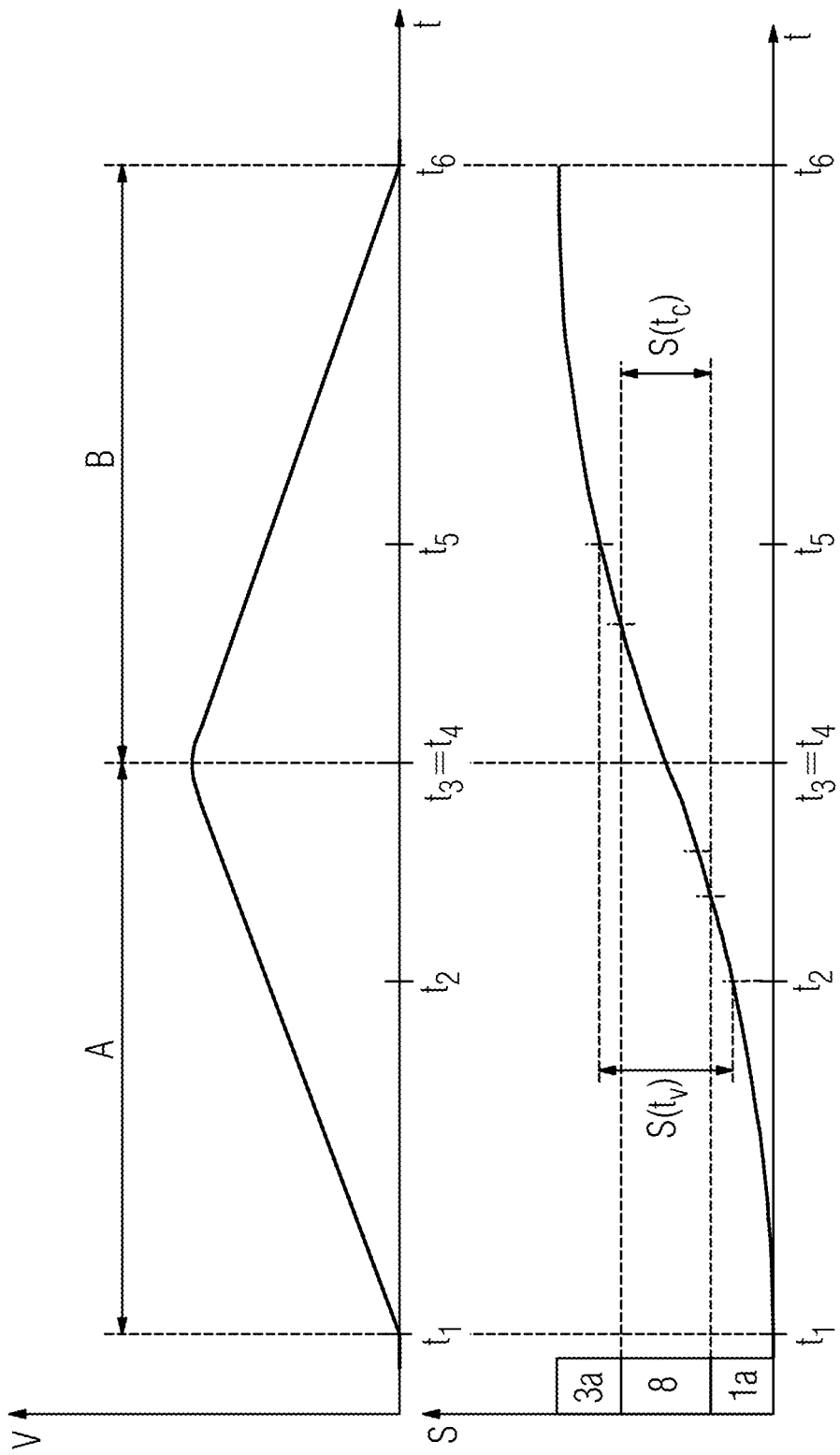

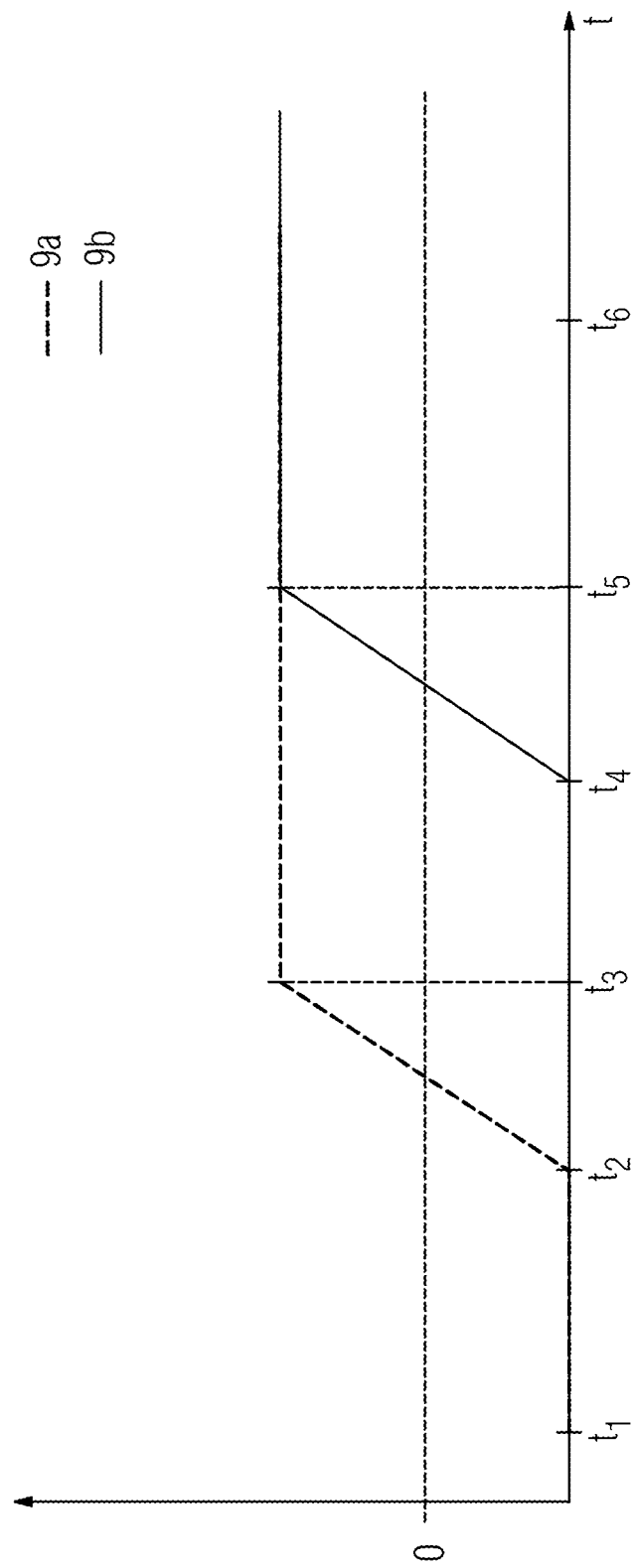

METHOD FOR RECORDING PROJECTIONS DURING A SPIRAL SCAN, METHOD FOR IMAGING AND MULTI-SLICE COMPUTED TOMOGRAPHY DEVICE

PRIORITY STATEMENT

The present application hereby claims priority under 35 U.S.C. §119 to German patent application number DE 102013215807.6 filed Aug. 9, 2013, the entire contents of which are hereby incorporated herein by reference.

FIELD

At least one embodiment of the invention generally relates to a method and medical imaging system for displaying image data.

BACKGROUND

A multi-slice computed tomography device is also denoted hereafter as a computed tomography device or as a CT device. In spiral CT, an examination object is moved continuously through a measurement field of a recording system along a system axis of the CT device by way of a table about which the recording system with at least one radiation source and a detector simultaneously executes a multiplicity of rotations. The beam of radiation of the radiation source thereby scans the object to be examined in the shape of a spiral, and a data volume is produced which is formed from a multiplicity of three-dimensional image elements. Image reconstruction and/or image processing methods subsequently enable a two- or three-dimensional representation of at least a part of the scanned region (ROI: Region of interest) of the examination object, which is normally used to make a diagnosis.

An important variable in spiral recordings is the table feed d during a complete revolution (360°) of the recording system. The greater the table feed d selected, the quicker a region of the examination object to be examined (ROI) can be scanned. If the table feed d selected is too large compared to the detector width D used, the beam of radiation does not scan all the volume elements of the region of the examination object to be examined, and the image quality deteriorates.

The relationship between the table feed d and the detector width D used is given by the so-called dimensionless pitch or pitch factor p. The pitch or pitch factor p specifies which distance the patient table has covered during a complete revolution of the recording system with reference to the detector width used. If a multi-slice computed tomography device with a multirow detector is used, for example, for spiral recording of N spiral slices of the same width S, the pitch or the pitch factor p is given by:

$$p = d/(N \cdot S). \quad (1)$$

Here, $N \cdot S$ is the width of the detector used for recording. In the typical clinical application of the spiral scan CT devices, and in the case of multi-slice spiral CT, it is common to use spirals with a constant pitch or pitch factor p of between 0.5 and 1.5 up to a maximum of 2.

The development of ever wider, multirow detectors with an enlarged cover in the direction of the system axis of the CT device, and the achievement of ever higher rotation times $T_{Rot}$ of the recording system has enabled the scanning times to be significantly reduced. However, this has the consequence that the speeds of the patient tables $V_U$ which are required and to be reached have not inconsiderably been increased.

If the acceleration of the patient table is not likewise increased, the problem arises that an ever larger acceleration distance is required for the table in order to bring the patient table up to the examination speed $V_U$ to be reached. The same problem arises with the slowing down of the patient table at the end of the examination, that is to say with the length of the braking distance which is required to brake the patient table to zero again from the examination speed $V_U$.

In addition, a fan-shaped beam geometry is used in a standard spiral scan. Whereas it is sufficient in a parallel beam geometry (for example, in the case of CT devices of the first and second generations with a pencil ray beam and a partial fan beam), to record projection recordings over an angle of 180° of the examination object, in order to be able to reconstruct a complete sectional image of the examination object, it is, by contrast, necessary in a fan beam geometry to carry out the projection recording over at least an angle of 180° plus the aperture angle α of the detector in a radial direction, in order to enable the reconstruction of a complete sectional image. In such a fan geometry, detectors typically have an aperture angle from approximately 60° to 90°, as a result of which there is a need for at least a projection recordings over a total angle of at least approximately 240° to 270° in order to be able to reconstruct a complete sectional image from a projection data record.

In order to be able to reconstruct the first sectional image of a selected examination region, there is thus a need for at least one projection recording over the total angle from at least approximately 240° to 270°, specifically before the patient table has reached the position of the start of the examination region. In order to be able to reconstruct the last sectional image of a selected examination region, there is likewise a need for at least one projection recording over the total angle of at least approximately 240° to 270°, specifically after the patient table has reached the position of the end of the examination region. In the standard spiral scan, the patient table moves at the examination speed $V_U$ during the entire recording. This means that a prerun scan and a postrun scan are required once the patient table has reached an examination speed $V_U$ and there is complete patient irradiation, in order to obtain the first and last sectional images of the examination region (R.O.I.). The length of the required prerun scan and the length of the required postrun scan are proportional to the examination speed $V_U$ of the patient table and to the rotational time $T_{Rot}$ of the recording system.

Given present patient tables with a fixed, maximum table travel distance, the consequence can be that the maximum available scanning region of the patient table is greatly reduced in some circumstances. This becomes clear, in particular, in the case of relatively wide detectors, since the length required for the prerun scan and the postrun scan increases. This becomes clear, likewise, with the relatively high examination speed $V_U$, since the acceleration distance and the braking distance likewise increase.

In some circumstances, the facts complicate, or even render impossible the use of fastening devices fitted to the table, the fastening devices further delimiting the available scanning region, as a result of which a deterioration in image quality is to be expected. One solution of the problem is in developing new tables which make available a longer total travel range and thereby enable a larger scanning region. However, this is connected by substantial development and production costs because the entire patient container apparatus has to be reconfigured. Moreover, more room for the travel range of the patient table is thereby required in the examination space.

SUMMARY

At least one embodiment of the present invention offers an improved solution to the problem.

At least one embodiment of the present invention is directed to a method for recording projections, a multi-slice computed tomography device, and/or a method for imaging.

The starting point of at least one embodiment is a computed tomography device which is suitable for spiral recording of a plurality of slices N. The respective slices of the computed tomography device preferably have a constant width S. Such a so-called multi-slice tomography device further has at least one radiation source which emits a beam emanating from a focus and has a detector array, opposite the focus, which supplies output data which represent the attenuation of the beams upon passage through an examination object arranged between the radiation source and the detector array. In this case, the detector preferably has detector elements arranged in matrix fashion which form columns and rows.

According to at least one embodiment of the invention, there is proposed a method for projection recording in the computed tomography device of the type mentioned at the start in which a patient table is moved through a measurement region of the computed tomography device, and time-resolved recording of projections of at least one part of an examination object moving with the table are carried out. In this case, the projection recording takes place at least partially during at least one phase of the variable patient table speed. The entire projection recording preferably takes place during one phase or during a plurality of phases of variable patient table speed.

Furthermore, during the at least one phase of variable speed of the patient table, the number of slices N(t) actually contributing to the recording is varied in such a way that the quotient $V_T(t)/N(t)$ formed from the current table speed $V_T(t)$ divided by the number of the slices N(t) contributing to the recording is constant or substantially constant. A substantially constant quotient $Q=V_T(t)/N(t)$ is understood to mean that the quotient can assume a value Q in a range of [Q−dQ; Q+dq], dQ being small compared to Q. In addition, the number of slices N(t) actually contributing to the recording, that is to say the number of the detector rows inserted at time t, for example, is recorded or determined in time-resolved fashion by the number of detector rows required to define a slice, at least during the at least one phase of variable patient table speed. The term number is understood in a broad sense here, and can be a number, that is to say a natural number, or a rational number, for example a fraction. In addition, the patient table position x(t) is recorded or determined at time t, that is to say in time-resolved fashion.

At least one embodiment of the invention further relates to a computed tomography device which can be used to carry out the projection recording method according to at least one embodiment of the invention. Such a computed tomography device is preferably a multi-slice computed tomography device and has at least one radiation source, at least one multirow detector and a device for dynamically varying the number of the slices contributing to the recording. Such a device for dynamically varying the number of the slices contributing to the recording is, for example, a diaphragm device for limiting the X-ray fan of the computed tomography device. In this case, each slice of the computed tomography device comprises at least one detector row of the detector. Such a computed tomography device enables the carrying out of a method according to at least one embodiment of the invention for projection recording given a constant pitch or pitch factor p and a variable speed of the patient table with the above-named advantages.

Finally, at least one embodiment of the invention relates to a computer software product in the form of programs or program modules, which implements at least a method of at least one embodiment when it is run on a computer device connected to a multi-slice computed tomography device. This enables the imaging of a data volume which has been obtained from a method according to at least one embodiment of the invention for projection recording, or with the aid of a computed tomography device according to at least one embodiment of the invention.

BRIEF DESCRIPTION OF THE DRAWINGS

The invention and further advantageous developments of the invention are explained in more detail below with the aid of the example embodiments illustrated schematically in the drawings, without a limitation of the invention thereby being imposed on the examples. Identical or functionally identical elements are provided in the figures with identical reference numerals. The illustrations in the figures are schematic and not necessarily true to scale.

In the figures:

FIG. 3 is a schematic of the relative dose, applied to the object to be examined, as a function of patient table position S(t);

FIG. 4 is a schematic of the patient table speed V(t) and the distance S(t) covered by the table as a function of time t for a spiral scan at a variable but maximum table speed V(t) and at a constant pitch p;

FIG. 5 is a schematic of the patient table speed V(t) and the distance S(t) covered by the table as a function of time t for a spiral scan at a variable, nonmaximum table speed V(t) and at a constant pitch p; and FIG. 6 is a schematic of the synchronous speed of at least one absorber element of a diaphragm device according to an embodiment of the invention for dynamically inserting and/or excluding the detector rows, contributing to the projection recording, of a computed tomography device.

DETAILED DESCRIPTION OF THE EXAMPLE EMBODIMENTS

Figure 1:
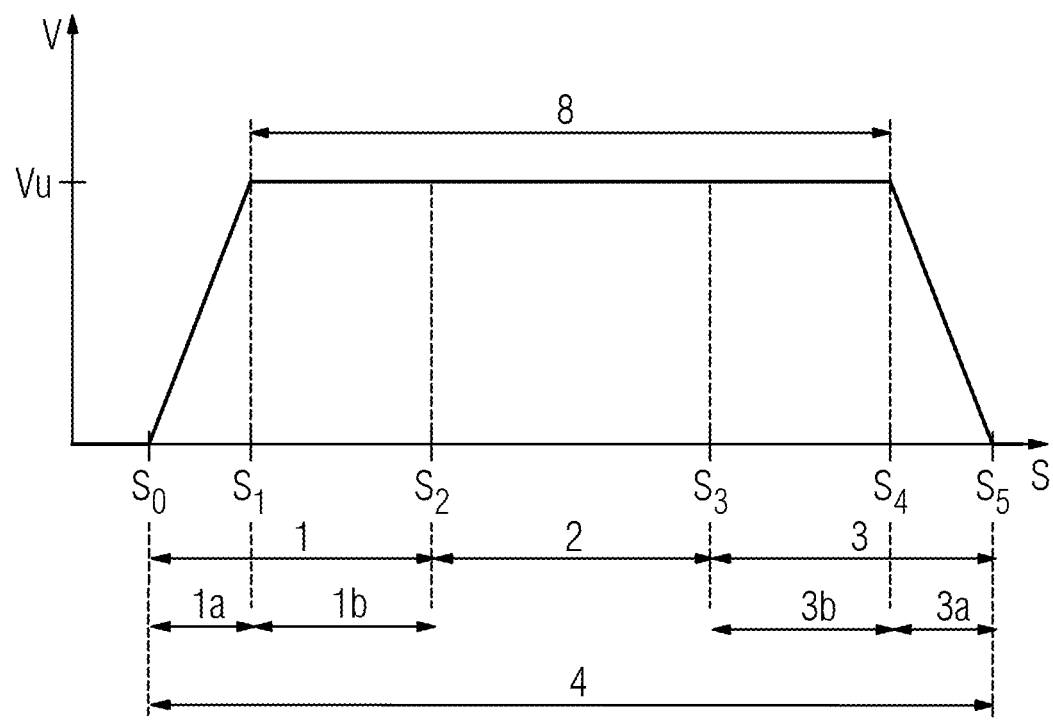
FIG. 1 is a schematic of the table speed as a function of the table position for a standard recording in a spiral scan.
Figure 1:
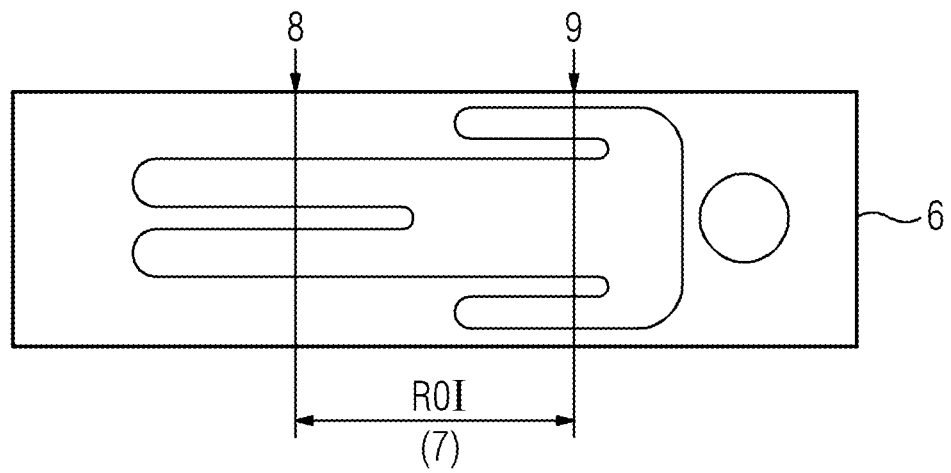

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The starting point of at least one embodiment is a computed tomography device which is suitable for spiral recording of a plurality of slices N. The respective slices of the computed tomography device preferably have a constant width S. Such a so-called multi-slice tomography device further has at least one radiation source which emits a beam emanating from a focus and has a detector array, opposite the focus, which supplies output data which represent the attenuation of the beams upon passage through an examination object arranged between the radiation source and the detector array. In this case, the detector preferably has detector elements arranged in matrix fashion which form columns and rows.

What is understood below by columns are the detector elements which are arranged along the system axis of the CT device and are arranged at the same angle. What is understood below by rows are the detector elements arranged radially with respect to the system axis of the CT device and are arranged at the same position along the system axis. In this case, the detector array can be of isotropic or anisotropic design, for example in the form of an adaptive array. Slices of prescribed width S which are to be scanned can in this case be formed by a plurality of detector rows, there being no need to use all the detector rows. The total width of the detector which is actually used can therefore deviate from the maximum width of the detector available in principle.

In the spiral scan run of today, an examination object is usually firstly positioned on a patient table and fixed as immovably as possible with the aid of fastening devices on the table. The patient table is accelerated up to the examination speed $V_U$ after selection and setting of the required scan parameters such as the end speed or examination speed of the patient table $V_U$ which is to be reached, the rotational time $T_{Rot}$ of the recording system which is to be reached and, in a multi-slice computed tomography device, the number of the scanning spirals N and their slice thickness or width S. After the acceleration phase of the patient table, the region of the examination object to be examined is spirally scanned with the aid of the X-ray fan while time-resolved projection recording is simultaneously performed at a constant patient table speed $V_U$ and constant rotation rate $T_{Rot}$. Upon termination of the spiral scanning and the projection recording, the patient table is finally stopped within a braking phase. As already explained above, the spiral scanning includes a prerun scan required for the completeness of the recording, and a postrun scan required for the completeness of the recording and whose length depends on the examination speed of the patient table and the rotation rate of the recording system.

Table 1 provides an overview regarding the acceleration distance, the prerun scan distance and the total prerun distance for different accelerations of the patient table. The calculation is based in this case on a constant collimation of N=76.8 mm, a rotational time of $T_{Rot}$=0.25 s and a rounding time of 100 ms.

| Pitch | Acceleration [mm/s$^2$] | $V_U$ [mm/s] | Acceleration distance [mm] | Prerun scan [mm] | Complete prerun [mm] |
|---|---|---|---|---|---|
| 0.5 | 300 | 154 | 47 | 29 | 76 |
| 1.0 | 300 | 308 | 173 | 57 | 230 |
| 1.5 | 300 | 462 | 377 | 65 | 442 |
| 0.5 | 1500 | 154 | 31 | 29 | 60 |
| 1.0 | 1500 | 308 | 77.5 | 57 | 135 |
| 1.5 | 1500 | 462 | 140 | 65 | 205 |

The complete prerun is the sum of the acceleration distance and the prerun scan distance. The prerun scan distance is proportional to the examination speed $V_U$ of the patient table, to the rotational time $T_{Rot}$ of the recording system and to the smaller of the factors a and b, in the case of which a=0.75 and b=(a/p+α/720°), α being the fan angle of the detector. The calculations apply in a symmetrical fashion for the total postrun distance, which is the sum of the braking distance and postrun scan distance.

As is to be seen from table 1, the acceleration distance is reduced by the increase in the patient table acceleration. However, the prerun scan distance remains independent of the examination speed $V_U$, and so the total prerun distance can be reduced thereby, although it is limited by the length of the prerun scan in the ideal case (with infinite acceleration).

At least one embodiment of the invention is based on the idea of carrying out at least some of the projection recording as early as during the acceleration phase and/or during the braking phase of the patient table. The scanning region available is thereby enlarged. Furthermore, it has been found that the simultaneous use of a constant pitch or pitch factor P of the entire projection recording simplifies the image reconstruction and/or the calculation of a data volume recorded in spiral mode and in a variable table speed $V_T(t)$. This procedure has two more advantages, which are explained below.

According to at least one embodiment of the invention, there is proposed a method for projection recording in the computed tomography device of the type mentioned at the start in which a patient table is moved through a measurement region of the computed tomography device, and time-resolved recording of projections of at least one part of an examination object moving with the table are carried out. In this case, the projection recording takes place at least partially during at least one phase of the variable patient table speed. The entire projection recording preferably takes place during one phase or during a plurality of phases of variable patient table speed.

Furthermore, during the at least one phase of variable speed of the patient table, the number of slices N(t) actually contributing to the recording is varied in such a way that the quotient $V_T(t)/N(t)$ formed from the current table speed $V_T(t)$ divided by the number of the slices N(t) contributing to the recording is constant or substantially constant. A substantially constant quotient $Q=V_T(t)/N(t)$ is understood to mean that the quotient can assume a value Q in a range of [Q−dQ; Q+dQ], dQ being small compared to Q. In addition, the number of slices N(t) actually contributing to the recording, that is to say the number of the detector rows inserted at time t, for example, is recorded or determined in time-resolved fashion by the number of detector rows required to define a slice, at least during the at least one phase of variable patient table speed. The term number is understood in a broad sense here, and can be a number, that is to say a natural number, or a rational number, for example a fraction. In addition, the patient table position x(t) is recorded or determined at time t, that is to say in time-resolved fashion.

Since the table feed d is a function of the table speed $V_T(t)$ and the rotational time $T_{Rot}$, namely $d=V_T(t)*T_{Rot}$, it follows from this on the assumption of a constant rotational time $T_{Rot}$ that the pitch or pitch factor p is also kept constant given a variable table speed $V_T(t)$. Given a variable table speed $V_T(t)$ and variable number of slices N(t) contributing to the recording, the pitch or pitch factor p is given by:

$$p=V(t)\cdot T_{Rot}/(N(t)\cdot S). \qquad (2)$$

As a result of this, the entire projection recording is performed given a pitch or pitch factor p which is constant, or substantially constant, the result being, inter alia, to enable a simplified image reconstruction. Here, the temporally varying table speed $V_T(t)$ is compensated for by a dynamic matching of the number of the slices N(t) contributing to the recording in such a way that the pitch or pitch factor remains constant or substantially constant. For example, the dynamic matching of the number of the slices N(t) contributing to the recording is varied by the insertion and exclusion or by the switching on and off of adjacent detector rows.

Such a method has the advantage of enabling projection recording in a spiral mode as early, for example, as during an acceleration process and/or a braking process of the patient table. A larger available scanning region is thereby enabled. Moreover, such a method enables the spiral scanning process to be configured otherwise than previously customary, for example as a sequence of phases of variable speeds with, or else also without an interposed phase of constant speed. In addition, the inventive method enables the use of known image reconstruction methods which presuppose a constant pitch or pitch factor p in a simple and known way. Furthermore, such a method has further advantages with regards to the dose usage and the signal-to-noise ratio, in particular in the direction of the system axis.

The result of this is, first and foremost, that the available effective scanning region of the table is increased and/or can be optimized. In contrast to the standard spiral recording at a constant table speed, in at least one embodiment of the inventive method the acceleration phase and the prerun scan and/or the braking phase and the postrun scan coincide at least partially. It follows that the length of the total prerun and/or the total postrun can be reduced, thereby enlarging the scanning region. It is preferably possible for the entire prerun scan to be included in the acceleration phase and/or the entire postrun scan to be included in the braking phase. Furthermore, it is possible thereby to prescribe a maximum length of the total prerun and/or postrun independently of all the parameters, and thereby to calculate and set the parameters required for the scan. It is ensured thereby that the distance covered by the table between the starting of the table and end of the prerun scan, and/or between the start of the postrun scan and the stopping of the table always remains smaller than the prescribed length of the prerun and/or of the postrun.

The acceleration phase and the prerun scan and/or the braking phase and the postrun scan coincide at least partially.

The prerun scan and/or the postrun scan are preferably included completely in the acceleration phase and/or in the braking phase. In both cases, it is possible to prescribe a maximum acceleration length and/or braking length which are intended to be available for the prerun phase composed of acceleration phase and prerun scan, and/or for the postrun phase composed of braking phase and postrun scan. It is possible therefrom to determine and set the parameters required for the scan such as table acceleration, rotation rate of the recording system, pitch or pitch factor p and temporal characteristic of the number of the detector rows contributing to the recording, so as to ensure a prescribed scanning region length to be determined in advance.

One advantageous development of the method according to at least one embodiment of the invention provides for the number of the slices N contributing to the recording to be varied in such a way that an examination object located at time t in the measurement region is exposed only to the radiation which is required for the number N(t) of the slices contributing to the recording. This is implemented, for example, by inserting or excluding adjacent detector rows, the insertion or exclusion being performed by a diaphragm device between the radiation source and the actual measurement region. Consequently, with the method according to the invention, all the data recorded contribute to the imaging such that no dose is applied unnecessarily, and no data of the data records need to be erased before the reconstruction. As a result, a reduction in the dose applied to the patient is achieved and the image reconstruction is simplified.

Furthermore, as a result thereof, the dose is applied homogeneously along the system axis of the computed tomography device in the examined volume. Compared to a spiral scan under the same conditions but with complete and constant collimation, this means a homogeneous dose distribution instead of a distribution with an up to three times higher relative dose at the start and at the end of the spiral scan. It is known that given the constant tube current the image noise depends strongly on the attenuation of the beams upon passage through the examination object arranged between the radiation source and the detector, the problem usually being addressed by a so-called automatic exposure control (AEC). Such an automatic exposure control reduces and homogenizes the image noise by a feedback-controlled tube current regulation such that the noise is kept substantially constant. Such an automatic exposure control for reacting to the shape and size of the object to be examined can be implemented entirely simply and as accustomed in the scope of the method according to the invention.

One advantageous development of the method according to at least one embodiment of the invention provides that the number of the slices N(t) contributing to the recording is determined at time t by the time-resolved recording or determination of a diaphragm position of a diaphragm device for limiting the X-ray beam of the computed tomography with the device. The result of this is that the number N(t) of the slices contributing to the recording can be extrapolated at any desired time t. This enables the determination of a continuous function N(t) which is thereby easier to integrate in an image reconstruction algorithm. If the diaphragm device is controlled in such a way that its temporal movement is known in advance, this thus enables a subsequent determination of the number of the slices N(t) contributing to the recording, as a result of which there is firstly a need to transmit fewer data.

A further advantageous development of at least one embodiment of the present invention provides that the length of the at least one phase of variable speed of the patient table is selected in such a way that during the at least one phase of variable speed of the patient table the recording system used for the projection recording is rotated by at least 180°+α, α being the aperture angle in a radial direction of the detector used in the method for projection recording relative to the radiation source. This ensures that the minimum data amount for image reconstruction, for example of the first and/or of the last sectional image of the examination region occurs during the at least one phase of variable speed of the patient table. As a result of this, the prerun scan and/or the postrun scan are included completely in the acceleration phase and/or in the braking phase. An optimized time/dose utilization therefore takes place as early as in the acceleration phase and/or braking phase, as does a simultaneous increase in the available scanning region.

A yet further advantageous development of the method according to at least one embodiment of the invention provides that the number N(t) of the slices contributing to the recording at time t is varied in stepwise, or quasi stepwise fashion. What is understood here by a "quasi-stepwise" change is generally a change which happens quickly compared to the time scale used, but with a finite value. By way of example, this can be performed by an appropriate temporal control of a diaphragm device for limiting the X-ray beam of the computed tomography device. For example, the diaphragm device executes a movement synchronous with the acceleration of the patient table. The result of this is that the number of the slices N(t) contributing to the recording at time t varies synchronously with the patient table position or movement in such a way that the pitch or pitch factor p remains constant or substantially constant. It is preferred for N(t) to be defined in advance. The number N(t) can therefore be determined in a time-resolved fashion without the need to extrapolate from the position determination or position recording of the diaphragm device, for example, for limiting the X-ray beam of the computed tomography device, as a result of which there is firstly a need to transmit fewer data.

A yet further advantageous development of the method according to at least one embodiment of the invention provides that the current table speed $V_T(t)$ is varied in stepwise or quasi stepwise fashion. As a result, the current table speed $V_r(t)$ can be determined in time-resolved fashion without the need to extrapolate from the table position, as a result of which there is firstly a need to transmit fewer data. It is also possible therefrom to perform the time-resolved determination of the patient table position. If, at the same time, the number of the slices N(t) contributing to the recording likewise varies in stepwise, or quasi stepwise fashion, the result is that the pitch or pitch factor p is constant at every time t. Furthermore, a continuous function can be approximated by selecting the width of the intervals between the individual steps.

A yet further advantageous development of the method according to at least one embodiment of the invention provides that the movement of the patient table has at least one phase of increasing speed and one phase of falling speed. In this case, the number of the slices N(t) contributing to the recording during the phase of increasing speed of the patient table is increased and the number of the slices N(t) contributing to the recording during the phase of falling speed of the patient table is reduced.

As a result, compared to a standard spiral scan, which has at least one acceleration phase, a prerun scan, a recording phase at constant table speed, a postrun scan and a braking phase, the method is optimized and can be carried out more simply. For example, the method according to at least one embodiment of the invention can consist only of two consecutive phases of variable speeds, the projection recording taking place during at least some of the respective consecutive phases of variable speeds. A maximum table utilization can be achieved as a result. In addition, the increase or the reduction in the number of the slices N(t) contributing to the recording happens during the phases of variable speeds, preferably in such a way that the sequence of the insertion of the individual slices and the sequence of the exclusion of the individual slices are identical. The latter ensures that the spiral length of the projection recording is of equal length for each slice, enables the recording of a complete image data record at the start and at the end of the scan, and simplifies the image reconstruction.

A yet further advantageous development of the method according to at least one embodiment of the invention provides that the movement of the table has at least one phase of constant speed during which all the slices provided for the recording contribute to the projection recording. The result of this is to enable at least a part of the projection recording at constant speed and a constant number of slices N contributing to the recording between phases of variable speeds, as with a standard spiral scan.

At least one embodiment of the invention further relates to a computed tomography device which can be used to carry out the projection recording method according to at least one embodiment of the invention. Such a computed tomography device is preferably a multi-slice computed tomography device and has at least one radiation source, at least one multirow detector and a device for dynamically varying the number of the slices contributing to the recording. Such a device for dynamically varying the number of the slices contributing to the recording is, for example, a diaphragm device for limiting the X-ray fan of the computed tomography device. In this case, each slice of the computed tomography device comprises at least one detector row of the detector. Such a computed tomography device enables the carrying out of a method according to at least one embodiment of the invention for projection recording given a constant pitch or pitch factor p and a variable speed of the patient table with the above-named advantages.

One advantageous development of the computed tomography device according to at least one embodiment of the invention provides that the computed tomography device according to the invention has at least one diaphragm device for limiting an X-ray beam of the computed tomography device, which diaphragm device has at least one absorber element movable linearly in one direction, and device for moving and dynamically regulating the speed of the at least one absorber element. A dynamic variation of the number of the slices contributing to the recording is thereby enabled. In this case, the diaphragm device is designed and arranged in the recording system in such a way that that the number of the detector rows irradiated by the radiation source can be dynamically varied by moving the absorber element. As a result, the number of the slices N(t) contributing to the recording can be controlled. The number of the slices contributing to the recording is preferably matched and/or synchronized with the position and/or the speed of the patient table.

A yet further advantageous development of the computed tomography device according to at least one embodiment of the invention provides that a change in the number of the detector rows irradiated by the radiation source is made by inserting or excluding at least one further adjacent detector row. As a result, the increase or reduction in the number of the detector rows contributing to the recording always takes place only in one direction of the detector width along the system axis of the computed tomography device. This enables the use of a simple diaphragm device with at least one linearly movable and moving absorber element for limiting the X-ray beam in order to vary the number of the detector rows contributing to the recording.

A further advantageous development of the computed tomography device according to at least one embodiment of the invention provides that the dynamic change in number of the detector rows irradiated by the radiation source is controllable by a control unit. The change is preferably controlled by moving the at least one absorber element as a function of at least one parameter at least partly varying with time. As a result, the collimation, that is to say the current number of the slices N(t) contributing to the recording, is, for example, variable as a function of the current table speed. In particular, it is possible thereby to couple the movement of the diaphragm device to the movement of the patient table. The movement of the diaphragm device is preferably at a speed which is proportional to the table speed, at least in the phases of the variable speed. In other words, the movement of the diaphragm device is synchronous with the table movement given a changed scaling of the speed to be used.

A yet further advantageous development of the computed tomography device according to at least one embodiment of the invention provides that the insertion device comprises a second absorber element which, with the aid of the device for moving and dynamic speed regulation, is movable linearly in the same direction as the first absorber element, but independently thereof. The result of this is that the detector rows contributing to the recording can be inserted or excluded in the same sequence, thus ensuring that the spiral length of the projection recording is of equal length for each slice so that the recording of a complete image data record at the start and at the end of the scan is complete for the image reconstruction, and the data records of all the slices are of the same length, which simplifies the image reconstruction.

A yet further advantageous development of the computed tomography device according to at least one embodiment of the invention provides that each absorber element has at least one adjustable end position in which the X-ray beam or X-ray fan of the respective absorber element is completely detected. As a result, the insertion device can be fitted in the beam path of the computed tomography device in such a way that the respective detector rows with the two absorber elements can be inserted and, above all, excluded in a targeted fashion such that the number of the slices contributing to the recording can be brought to zero at the start and at the end of the scan. The adjustable positioning of the respective end position furthermore enables matching with various devices or device settings, for example when the maximum number or the width of the individual slices is to be changed between two different scanning processes.

A yet further advantageous development of the computed tomography device according to at least one embodiment of the invention provides that the second movable absorber element is fixable with the aid of the first absorber element in such a way that a slit of defined width can be set between the two absorber elements. As a result, in order to enable the respective detector rows to be inserted and excluded during a phase of variable speed of the patient table, it is necessary for the insertion device to be moved from the at least two absorber elements fixed to one another between the two end positions of the respective absorber elements only in one direction linearly at an appropriate speed.

A yet further advantageous development of the computed tomography device according to at least one embodiment of the invention finally provides that the insertion device is arranged upstream of the radiation source. As a result, the examination object located in the measurement region is illuminated only when a projection recording is also taking place. As a result, a dose reduction, in particular at the start and at the end of the scan, is enabled. In addition, compared to a spiral scan with at least partially variable speed but with a constant and complete collimation, a homogeneous dose is thereby applied in the examined volume along the system axis of the computed tomography device instead of a dose distribution with an up to three times higher relative dose at the start and at the end of the spiral scan. In this way, all the recorded data contribute to the imaging such that no dose is applied unnecessarily. An optimum use of the applied dose is performed in this way with the image quality being obtained at the same time.

At least one embodiment of the invention relates, furthermore, to a method for imaging from a data volume which has been recorded with the aid of the above-mentioned method for projection recording.

Such a method according to at least one embodiment of the invention is based on a weighted, filtered back-projection of the recording data. Weighted, filtered back-projection methods (WFBP) in the CT imaging take account of so-called cone beam artifacts which are caused by the non-parallelism of the beams used during the recording, and redundancy artifacts which can be produced by multiple irradiation of one and the same voxel in the case of spiral scans. Such a method is, for example, presented in Stierstorfer et al.: "Weighted FBP—a simple approximate 3D FBP algorithm for multi-slice spiral CT with good dose usage for arbitrary pitch", Phys. Med. Bio. 49, 2004, pp. 2209-2218. In the imaging method according to the invention, it is proposed in this case that the temporally varied number of the slices N(t) contributing to the recording be taken into account computationally during the at least one phase of variable table speed by modifying the weighting factor W(q) in the weighted, filtered back-projection in the course of back-projection by replacing the slice index q, corresponding to the z-coordinate, in the weighting factor W(q) by a modified slice index q* which is equal to the slice index q corresponding to the z-coordinate times the quotient NMax/N(t) formed from the maximum number of the slices NMax used divided by the number N(t) of the slices which are actually contributing to the recording at time t. The altered weighting factor W(q*) is therefore written as:

$$W(q^*) = \begin{cases} 1 & \text{for } |q^*| < Q \\ (\cos(\Pi/2 \cdot (|q^*|-Q)/(1-Q)) & \text{for } Q \le |q^*| < 1, \\ 0 & \text{otherwise} \end{cases} \quad (3)$$

where $q^* = N_{Max}/N(t) \cdot q$ and in which q is the normalized number of the active detector rows, that is to say a number between 0 and 1. Q is a free parameter which fixes when the weighted function is attenuated in the direction of the row. The value is typically 0.8, and is selected such that cone beam artifacts do not occur as far as possible.

An advantageous development of the method according to at least one embodiment of the invention provides a pretreatment step of the recorded data volume in the case of which a consistent data record of parallel data from the data volume for an arbitrary imaging position along a scanning direction defined by the table movement is generated, the variable table speed during the at least one phase being taken into account computationally for the data recorded during the at least one phase. Thereby taking into account in the so-called z-interpolation, which precedes the known back-projection with or without convolution on the projection data, that the projection recording has taken place at different speeds in the at least one phase of variable speed. The calculation of a record of parallel data for an arbitrary table position is thereby enabled.

A further advantageous development of the method according to at least one embodiment of the invention provides that the table speed variable during the at least one phase is calculated by a numerical differentiation of the recorded table positions. This enables the extrapolation of the table speed and, if appropriate, the use of a continuous function in at least one embodiment of the imaging method, thus the method is simplified.

Finally, at least one embodiment of the invention relates to a computer software product in the form of programs or program modules, which implements at least a method of at least one embodiment when it is run on a computer device connected to a multi-slice computed tomography device. This enables the imaging of a data volume which has been obtained from a method according to at least one embodiment of the invention for projection recording, or with the aid of a computed tomography device according to at least one embodiment of the invention.

FIG. 1 is a schematic of the table speed V as a function of the table position S for a standard recording at a constant table speed in a spiral scan. The table speed V is plotted in the upper part as a function of the table position S. The standard spiral scan in this case has various phases 1, 1a, 1b, 2, 3, 3a and 3b, which are sketched in the middle part of the illustration. Finally, the lower part is a schematic of an object 5 to be examined, which is mounted on a patient table 6.

The patient table is accelerated from the rest position S0 to an examination speed $V_U$ during phase 1a. The patient table covers a distance S0S1 during the phase. The projection recording starts once the patient table has reached the target speed $V_U$. Subsequently, the patient table travels further at the speed $V_U$ and covers a distance S1S4 before, after the projection recording has been terminated, being braked again in the last phase 3a within the distance S4S5. The phase of constant table speed consists in this case of three different phases 1b, 2 and 3b. Projections are recorded continuously during all three phases. The data information required in order to be able to reconstruct the first sectional image of the examined region is collected during phase 1b. The distance S1S2 therefore amounts to at least $T_{Rot}*V_U*$min (a, b). Data information required in order to be able to reconstruct the last sectional image of the examined region is collected during phase 3b. The distance S3S4 therefore amounts to at least $T_{Rot}*V_U*$min (a, b). The data information required in order to be able to reconstruct the remaining examined region, that is to say in order to be able to reconstruct the volume of the examination object between the first and the last sectional images, is collected during phase 2. The so-called prerun phase 1 comprises phases 1a and 1b. The so-called post run phase 3 comprises phases 3a and 3b. The patient table 6 must cover at least the distance S in order to obtain sufficient data information for the reconstruction of the region 7 to be examined, including first and last sectional images 8, 9. A projection recording takes place during the complete phase 8.

Figure 2:
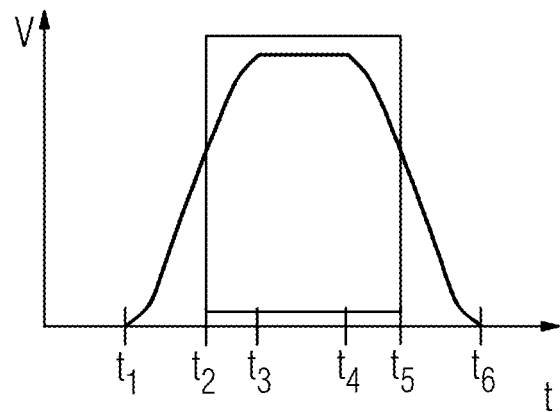
FIG. 2 is a schematic of the table speed V, the number of the slices N contributing to the projection recording, and the pitch p as a function of the time t for a method according to an embodiment of the invention.
Figure 2:
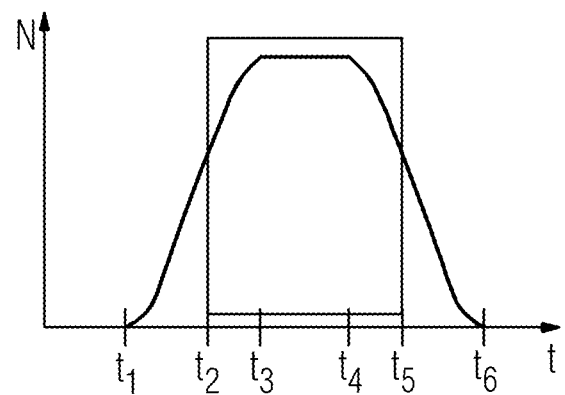
Figure 2:
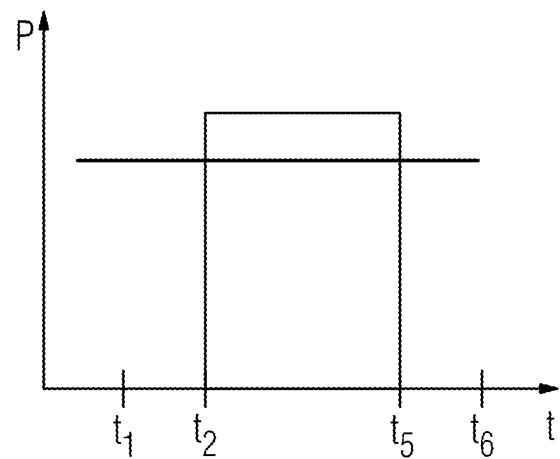

FIG. 2 is a schematic of the table speed during a spiral scan, the data recording, symbolized here by the rectangle partly at a variable speed V(t) of the patient table, being recorded and the collimation N(t) being varied in such a way during the recording that the pitch or pitch factor p is kept constant: $p = V(t) \cdot T_{Rot}/(N(t) \cdot S)$. In this case, the table speed V(t), the collimation, that is to say the number of the slices N(t) contributing to the projection recording, and the pitch or pitch factor p are plotted as a function of time. In this case, t1 denotes the time at which the table starts to accelerate, t2 the time at which the projection recording starts, t3 the time at which the patient table 6 has reached its maximum speed $V_U$, t4 the time at which the patient table 6 starts to brake, t5 the time at which the projection recording is terminated, and t6 the time at which the patient table is in the rest position again.

FIG. 3 is a schematic of the relative dose σ applied to the object to be examined as a function of the patient table position S(t) for two spiral scans which are recorded at least partially at a variable speed V(t) of the patient table, the first curve illustrating a spiral scan with full collimation (upper curve) and the second curve illustrating a spiral scan at a constant pitch or pitch factor p by dynamically switching on and off the slices N(t) contributing to the recording. Obviously, the curve of the spiral scan which was recorded given full, constant collimation has a much higher value (approximately three times the value) at the start and at the end of the table movement compared to the spiral scan in accordance with the method according to the invention.

FIG. 4 is a schematic of the patient table speed V(t) and of the distance S(t) covered by the table as a function of time t in the case of a spiral scan with two phases A, B of variable table speed V(t), and a phase C of constant table speed and a constant pitch p. The number of the slices N(t) contributing to the projection recording is varied as a function of the patient table speed V(t) between t1 or t2 and t3 and between t4 and t5 or t6, such that the pitch or pitch factor remains constant during the projection recording. If the maximum table speed is selected to be equal to the target speed for a standard scan, and the pitch or pitch factor p is selected to be equal in both cases, a very similar number results in the two cases of the scanning time $T_C$ and $T_V$, $T_C$ being the conventional scanning time and $T_V$ the scanning time at a variable speed. By way of example, in the case of a detector with 128 rows of 0.6 ram thickness, that is to say a maximum collimation of 76.8 mm and a length of the image volume of 150 mm, the scanning time for a maximum table speed of approximately 275 mm/s and with a pitch of 0.9 is $T_C$=0.54 s for a standard scan and $T_V$=0.55 s for a spiral scan according to an embodiment of the invention.

FIG. 5 is a schematic of the patient table speed V(t) and of the distance S(t) covered by the table as a function of time t for a spiral scan at a variable, non-maximum table speed V(t) for the two phases A, B of the variable table speed and a constant pitch p. In this case, the pitch or pitch factor p is selected to be greater than in FIG. 4. The number of the slices N(t) contributing to the projection recording is varied between t1 or t2 and t3 and between t4 and t5 or t6 as a function of the patient table speed V(t), that is to say during the entire projection recording, so that the pitch or pitch factor remains constant during the projection recording. If the maximum table speed reached is selected to be equal to the target speed for a standard scan, and the pitch or pitch factor p is selected to be equal in both cases, a higher number than the conventional scanning time $T_c$ results for the scanning time $T_V$ in the case of the spiral scan at a variable table speed. By way of example, in the case of a detector with 128 rows of 0.6 mm thickness, that is to say a maximum collimation of 76.8 mm and a length of the image volume of 150 mm, the scanning time for a maximum table speed of approximately 460 mm/s and with a pitch of 1.5 is $T_c$=0.32 s for a standard scan and, at a maximum table speed of approximately 315 mm/s, $T_V$=0.53 s for a spiral scan according to the invention.

FIG. 6 is a schematic of a possible movement $S_A$, synchronous with the patient table, of the two absorber elements (upper and lower curve, respectively) of a diaphragm device with two absorber elements 9a, 9b, which can move relative to one another, for dynamically inserting and/or excluding the detector rows, contributing to the projection recording, of a computed tomography device as a function of time t during a spiral scan at a constant pitch, but at least partially variable table speed. The maximum speed of the absorber elements is reduced by approximately half compared to a standard spiral scan. It is therefore possible in principle to make use of the diaphragms already included in a standard spiral CT device. It is possible to follow travel curves with a slightly varying profile for the purpose of optimization.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred exemplary embodiment, the invention is not limited by the disclosed examples and other variations can be derived herefrom by the person skilled in the art, without departing from the scope of protection of the invention.

What is claimed is:

1. A method for recording projections during a spiral scan with a multi-slice computed tomography device, the method comprising:
    moving a patient table through a measurement region of the multi-slice computed tomography device, the moving of the patient table including at least one phase of variable speed during the projection recording;
    determining, as a function of time, a position of the patient table;
    recording, as a function of time, the projections of at least one part of an examination object moving with the patient table, a number of slices of a detector contributing to the recording during the at least one phase of variable speed of the patient table being varied as a function of the variable speed of the patient table such that a quotient formed from a current value of the variable speed of the patient table divided by the number of the slices contributing to the recording of the projections is constant resulting in a constant pitch factor during the recording; and
    determining, as a function of time, the number of the slices contributing to the projection recording.

2. The method of claim 1, further comprising:
    applying a dose of radiation to the examination object homogenously along a system axis of the multi-slice computed tomography device.

3. The method of claim 2, wherein the number of the slices contributing to the recording is varied such that the examination object located in the measurement region is exposed only to radiation required for the number of the slices contributing to the recording.

4. The method of claim 2, wherein the determining the number of the slices includes recording a time-based position of a diaphragm device for limiting an X-ray beam of the multi-slice computed tomography device.

5. The method of claim 1, wherein the number of the slices contributing to the recording is varied such that the examination object located in the measurement region is exposed only to the radiation required for the number of the slices contributing to the recording.

6. The method of claim 1, wherein the determining the number of the slices includes recording a time-based position of a diaphragm device for limiting an X-ray beam of the multi-slice computed tomography device.

7. The method of claim 1, wherein a length of the at least one phase of variable speed of the patient table is selected such that, during the at least one phase of variable speed of the patient table, a recording system used for the recording of the projections is rotated by at least 180°+α, α being an aperture angle in a radial direction of a detector of the recording system relative to a radiation source.

8. The method of claim 1, wherein the number of the slices contributing to the recording is varied in a stepwise fashion.

9. The method of claim 1, wherein the current value of the variable speed of the patient table is varied in a stepwise fashion.

10. The method of claim 1, wherein the moving moves the patient table by increasing a speed of the patient table during at least a first phase and decreasing the speed of the patient table during at least a second phase, the number of the slices contributing to the recording being increased during the first phase of increasing speed, and the number of the slices contributing to the recording being decreased during the second phase of decreasing speed such that a sequence of insertion of individual ones of the number of slices and a sequence of exclusion of individual ones of the number of slices are identical.

11. The method of claim 1, wherein the moving moves the patient table at a constant speed for at least one phase during the recording, in a case where all the slices contribute to the projection recording.

12. A method for imaging a data volume recorded according to the method of claim 1, based on a weighted, filtered back-projection of the recorded data, the method comprising:
modifying, during a back-projection, a weighting factor in the weighted, filtered back-projection based on the varied number of the slices contributing to the recording during the at least one phase of variable speed of the patient table.

13. The method of claim 12, wherein the modifying modifies the weighting factor by replacing a slice index corresponding to a z-coordinate in the weighting factor by a modified slice index which is equal to the slice index corresponding to the z-coordinate times a quotient formed from a maximum number of the slices used divided by a number of the slices actually used.

14. The method of claim 12, further comprising:
generating a consistent data record of parallel data from the data volume for an arbitrary imaging position along a scanning direction defined by the movement of the patient table, the variable speed of the patient table during the at least one phase being taken into account computationally for the data recorded during the at least one phase.

15. The method of claim 12, wherein variations in the speed of the patient table during the at least one phase is determined by a numerical differentiation of the recorded patient table positions.

16. A non-transitory computer readable medium comprising computer-readable instructions, which when executed by a processor, cause the processor to control a multi-slice computed tomography device to implement the method of claim 12.

17. A non-transitory computer readable medium comprising computer-readable instructions, which when executed by a processor, cause the processor to control a multi-slice computed tomography device to implement the method of claim 1.

18. A multi-slice computed tomography device, comprising:
at least one recording system;
an insertion device configured to limit an X-ray beam of the multi-slice computed tomography device, the insertion device including,
at least one first absorber element configured to move linearly in one direction, and
a device configured to move and dynamically regulate a speed of the at least one first absorber element, the insertion device being designed and arranged in the at least one recording system such that a number of detector rows of a detector irradiated by a radiation source is dynamically variable by moving the at least one first absorber element; and
a controller configured to control a dynamic change, in the number of the detector rows irradiated by the radiation source, by controlling the movement of the at least one first absorber element as a function of at least one time-dependent parameter such that a quotient formed from a current value of a variable speed of a patient table of the multi-slice computed tomography device divided by a number of the detector rows contributing to a recording of projections by the multi-slice computed tomography device is constant resulting in a constant pitch factor during a recording session.

19. The multi-slice computed tomography device of claim 18, wherein the controller is configured to control the dynamic change in the number of the detector rows irradiated by the radiation source by inserting a detector row into the number of the detector rows or excluding a detector row from the number of the detector rows.

20. The multi-slice computed tomography device of claim 19, wherein the insertion device comprises at least one second absorber element configured to linearly move, via the insertion device, in the same direction as the at least one first absorber element, but independently thereof.

21. The multi-slice computed tomography device of claim 20, wherein each of the at least one first and second absorber elements includes at least one adjustable end position in which the X-ray beam of the computed tomography device is completely absorbed by a respective one of the at least one first and second absorber elements.

22. The multi-slice computed tomography device of claim 18, wherein the insertion device comprises at least one second absorber element configured to linearly move, via the insertion device, in the same direction as the at least one first absorber element, but independently thereof.

23. The multi-slice computed tomography device of claim 22, wherein each of the at least one first and second absorber elements includes at least one adjustable end position in which the X-ray beam of the computed tomography device is completely absorbed by a respective one of the at least one first and second absorber elements.

24. The multi-slice computed tomography device of claim 22, wherein the at least one second absorber element is configured to be fixed relative to the at least one first absorber element in such a way that a slit of defined width is set between the at least one first and second absorber elements.

25. The multi-slice computed tomography device of claim 18, wherein the insertion device is arranged upstream relative to the radiation source.

* * * * *